(12) United States Patent
DeAngelo et al.

(10) Patent No.: US 8,156,784 B2
(45) Date of Patent: Apr. 17, 2012

(54) SYSTEM AND METHOD FOR DERIVATION AND REAL-TIME APPLICATION OF ACOUSTIC V-PATH CORRECTION DATA

(75) Inventors: Paul Joseph DeAngelo, West Bridgewater, MA (US); Steven Abe LaBreck, Boston, MA (US)

(73) Assignee: Olympus NDT, Inc., Waltham, MA (US)

( * ) Notice: Subject to any disclaimer, the term of this patent is extended or adjusted under 35 U.S.C. 154(b) by 350 days.

(21) Appl. No.: 12/631,065

(22) Filed: Dec. 4, 2009

(65) Prior Publication Data

US 2011/0132067 A1 Jun. 9, 2011

(51) Int. Cl.
*G01B 17/02* (2006.01)
(52) U.S. Cl. .......................... 73/1.82; 73/597
(58) Field of Classification Search ............ 73/1.82, 73/597, 602, 627
See application file for complete search history.

(56) References Cited

U.S. PATENT DOCUMENTS

| | | | | |
|---|---|---|---|---|
| 4,570,486 A | * | 2/1986 | Volkmann | 73/597 |
| 4,615,217 A | * | 10/1986 | Koike et al. | 73/624 |
| 4,680,960 A | * | 7/1987 | Yamanaka et al. | 73/114.29 |
| 5,156,636 A | * | 10/1992 | Kuljis | 73/597 |
| 5,349,862 A | * | 9/1994 | Chubachi et al. | 73/602 |
| 5,513,531 A | * | 5/1996 | Sapia et al. | 73/602 |
| 5,549,001 A | * | 8/1996 | Brokowski et al. | 73/597 |
| 5,608,165 A | * | 3/1997 | Mozurkewich, Jr. | 73/599 |
| 5,723,791 A | * | 3/1998 | Koch et al. | 73/597 |
| 6,078,397 A | * | 6/2000 | Monchalin et al. | 356/503 |
| 6,282,962 B1 | * | 9/2001 | Koch et al. | 73/602 |
| 7,272,529 B2 | * | 9/2007 | Hogan et al. | 702/171 |
| 7,980,142 B2 | * | 7/2011 | Nakabayashi et al. | 73/861.27 |

FOREIGN PATENT DOCUMENTS

WO   WO2009141360   * 11/2009

* cited by examiner

*Primary Examiner* — J M Saint Surin
(74) *Attorney, Agent, or Firm* — Ostrolenk Faber LLP

(57) ABSTRACT

A system and method for carrying out non-destructive testing and inspection of test objects to assess their structural integrity uses a calibration module configured to provide V-Path time of flight (TOF) correction data over a plurality of object thickness points, obtained from an object or objects having known thicknesses using the same physical probe as is used for the inspection measurements. When a probe launches acoustical waves into a test object and an instrument and a control system compute a time of flight value of the acoustical waves launched by the probe, the pre-obtained V-Path TOF correction data is used to correct the measured time of flight computed by the instrument.

19 Claims, 9 Drawing Sheets

SYSTEM AND METHOD FOR DERIVATION AND REAL-TIME APPLICATION OF ACOUSTIC V-PATH CORRECTION DATA

FIELD OF THE INVENTION

The present invention relates to non-destructive testing and inspection systems (NDT/NDI) and more particularly to a method to compensate for acoustic V-Path time of flight errors and thereby optimize inspection measurement accuracy.

BACKGROUND OF THE INVENTION

The measurement data from NDT/NDI devices used for the routine monitoring of structural integrity must be of sufficient accuracy to allow a valid assessment to be made of the condition of the structure under test. Examples of such structures are pipes and vessels widely used in the petrochemical and other industries. Examples of measurement data are pipe wall thickness and other geometric conditions, including, but not limited to, the presence of irregular surfaces (e.g. corrosion, oxide, etc.) and flaws (e.g. porosity, cracks, etc.).

The decision to perform or not perform maintenance on a structure is made based on the assessment of the measurement data. Therefore, the measurement accuracy will have a direct impact on the decision. The consequence of inaccurate measurement data that underestimates an unfavorable condition of a structure can result in failures occurring before maintenance is performed. Conversely, inaccurate measurement data that overestimates an unfavorable condition of a structure can result in performing expensive and unnecessary maintenance.

One of the most common NDT/NDI devices used for assessing structural integrity is a corrosion gage, such as the instant assignee's 37 DLP product. Products of this type typically employ a 'dual-element' probe or probe system that contains one element for acoustic transmission and another for acoustic reception, preferably packaged in an integral housing. The two elements are set at a fixed angle, thereby setting a fixed focal depth and 'V-Path' within the object being tested. Although this element positioning provides advantages for measuring corrosion wear, measurement errors, known as 'V-Path errors', can be introduced when measuring thicknesses at depths other than that of the focal depth.

The specific challenge herein dealt with is to provide a method that will ameliorate the measurement errors resulting from V-Path echo, which is the energy path traveled by the acoustic wave after the energy is transmitted into the target material and reflected from the back-wall of the material and into the receive element of the transducer. Particularly, V-Path errors occur when thickness measurements are being made on a material thinner than the focal thickness of the transducer.

Existing efforts have been made to eliminate or reduce such errors as described above. Thus, embodiments employing pre-defined data for the V-Path, or time distortion, correction in the calculation of a thickness measurement are well known by those skilled, and are therefore not described in detail herein.

One conventional solution for V-Path error compensation employs pre-defined static data tables to compensate for the time distortion; however, this solution has the drawback of not accounting for actual material sound velocity, transducer wear and manufacturing variances in transducer population.

Materials under inspection have their own individual velocities denoted as V, where V=material velocity. U.S. Pat. No. 3,554,013 teaches a hardware error correction circuit for ultrasonic thickness gauges. It is not a software method and presents the drawbacks of thermal and other electronic drift and material costs.

U.S. Pat. No. 4,570,486 teaches V-Path calibration for UT thickness measurement using hardware error correction circuits for ultrasonic thickness gauges. It is not a software method and presents the drawbacks of thermal and other electronic drift and material costs.

Current V-Path methods using a pre-determined data table, called "V-Path Table," use empirical methods of deriving data to generate the Table. The predetermined Table is generated by using TOF measurement methods on a batch of typical transducers of one model. It is then used for hundreds of the transducers of the same model for many years. The existing V-Path Table is herein referred to as the "Empirical V-Path Table".

Using an Empirical V-Path Table to compensate all the transducers of one model is less accurate because of variations of transducer factors such as acoustical focal depth and saturation of the acoustic barrier. The factors causing such variations include manufacturing tolerance changes in different batches of transducers, changes in material characteristics, and changes caused by wear-and-tear.

Accordingly, a solution that overcomes the drawbacks described above and results in advantages highly valued by potentially affected industrial and public infrastructure concerns, needs to:

a. Improve measurement accuracy;
b. Extend the longevity of transducers along with their measurement accuracy; and
c. Improve measurement accuracy of generic transducers for which the pre-defined V-Path data is unknown.

SUMMARY OF THE INVENTION

Accordingly, it is an object of the present invention to provide a system and method for obtaining more accurate V-Path correction data.

It is a further object of the invention to provide a system and method that is able to extend the longevity of proprietary transducers and their measurement accuracy.

Yet another object of the invention is to provide a system and method to improve measurement accuracy of generic transducers for which a pre-defined V-Path correction data is unknown.

The foregoing and other objects of the invention are realized with a thickness measuring system for measuring the thicknesses of test objects. The system includes a calibration module which is configured to provide V-Path time of flight (TOF) correction data over a plurality of object thickness points, obtained from one or more objects having known thicknesses. A probe configured to launch acoustical waves into a test object and to receive returning waves is employed, to produce an electrical output representative of the returning waves. An instrument, including control and computation hardware and software, is coupled to the probe and is configured to compute a time of flight value of the acoustical waves launched from the probe. A correction module associated with the instrument and configured to receive the V-Path TOF correction data from the calibration module is used to correct the time of flight computed by the instrument, based on the V-Path TOF correction data provided by the calibration module.

In accordance to various embodiments of the system and method of the present disclosure, the probe is preferably a dual element probe. Further, the V-Path TOF correction data can be provided in the form of a plurality of discreet correction values and those values can be used to compute correction values, needed to correct the TOF in real-time as the measurement is being made. Alternatively, linear equations or higher order polynomials can be fitted to the V-Path TOF correction data and these equations can be used to compute the needed TOF correction information in real-time as the measurement is being made.

Other features and advantages of the present invention will become apparent from the following description of the invention that refers to the accompanying drawings.

DETAILED DESCRIPTION OF THE INVENTION

Figure 1:
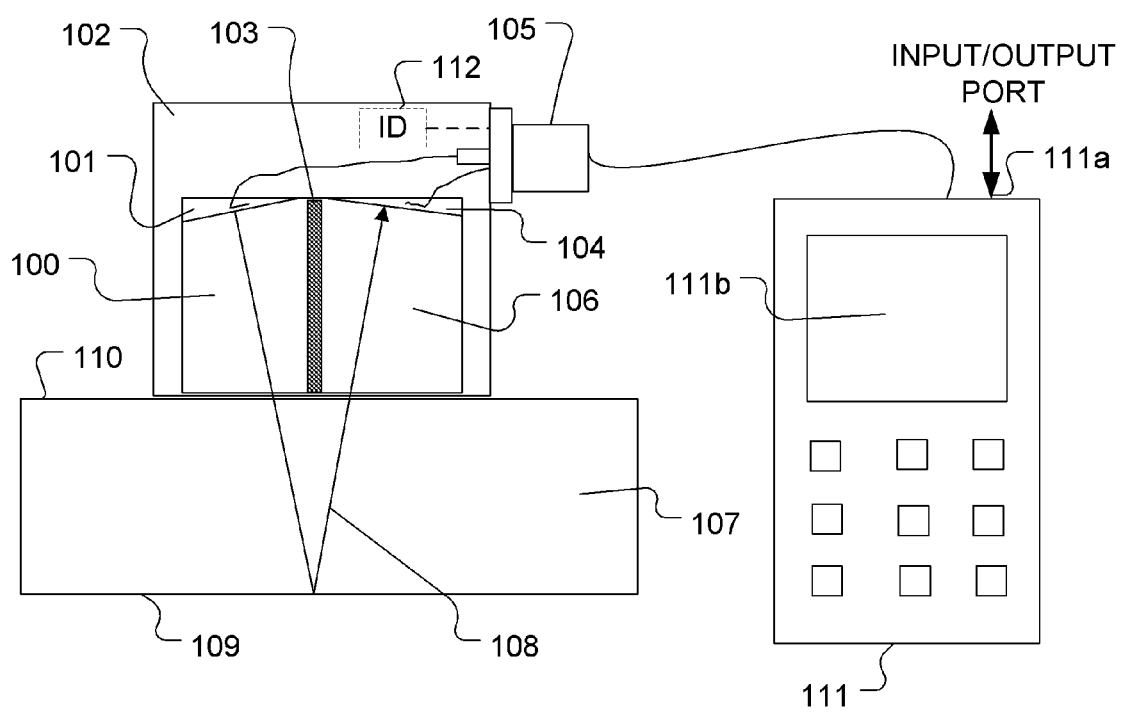
FIG. 1 is a diagram of a Dual Element Ultrasonic Transducer depicting the Effective Angular Sound Energy Path for Thick Material targets after the Transducer has been electrically excited by the UT apparatus.
Figure 2:
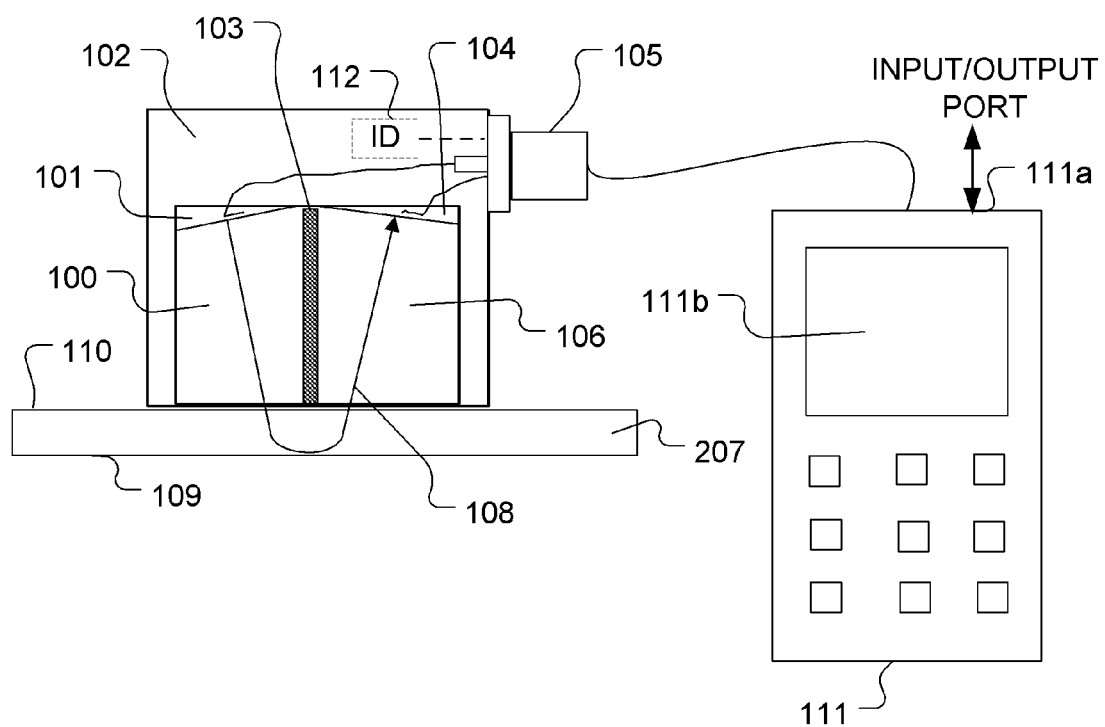
FIG. 2 is a diagram of a Dual Element Ultrasonic Transducer depicting the Effective Angular Energy Sound Path for Thin Material targets after the Transducer has been electrically excited by the UT apparatus.
Figure 3:
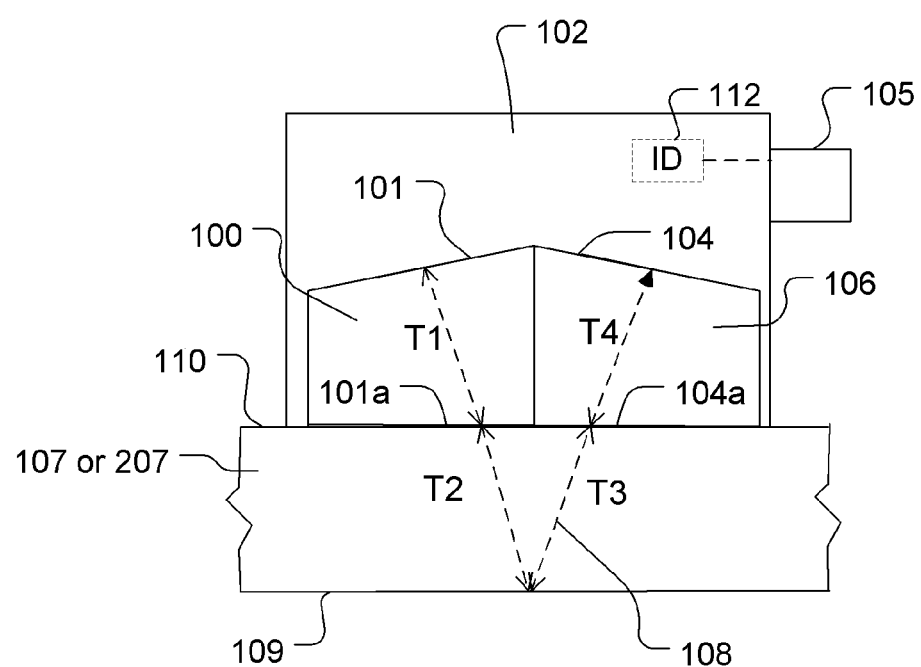
FIG. 3 is a diagram showing the Measured Time Intervals that comprises a Time Of Flight measurement for a Dual Element Ultrasonic Transducer.

In order to assist the understanding of presently disclosed V-Path error calibration method, the following description is given in association with background FIGS. 1-3.

It should be noted that 'sensor', 'probe' and 'transducer' are herein used in the present disclosure interchangeably. The term 'real-time measurement' is used in the present disclosure to mean the immediate measurement result provided to the user or external device by measurement device 111 (FIGS. 1 and 2) using one or more probe excitation/response cycles. The measurement result may be provided to the user by means of display 111b, an integral audio device (not shown), and/or an external device by means of input/output port 111a. The measurement result may be comprised of, but not limited to, values representing thickness, relative thickness and/or an alarm indication.

Referring to FIG. 1, the presently disclosed V-Path error compensation method as disclosed in used in conjunction with a dual-element transducer ultrasonic inspection system. The inspection system comprises a transducer 102; a measurement device 111 wherein the algorithm of the present disclosure is executed; and a target test object 107.

The invention is a system and method employing a software program that may be used for producing, and employing time distortion correction data, henceforth referred to as a V-Path Table for probes, that may be employed by ultrasonic thickness measuring apparatus. Ultrasonic thickness measuring apparatus will henceforth be referred to as measurement device 111. It should noted that although the preferred embodiment of the present disclosure describes an exemplary ultrasonic measuring apparatus, the teachings of the present disclosure may be applied at acoustic frequencies below the ultrasonic range (typically <20 kHz).

V-Path correction data may be used in the measurement calculation when the need to compensate for time distortion introduced by Angular Sound Energy Paths is required. Refer to the Effective Angular Sound Energy Paths 108 in FIG. 1 and FIG. 2. Note that the effective Angular Sound Energy Path distortion is greater in thin material targets 207 FIG. 2, than that of thick material targets 107 of FIG. 1. Thus, as shown by curve 802 of FIG. 8, time distortion effects increase as the thickness of the target material decreases when V-Path correction is not present. Hence, the application of V-Path correction factor, $t_v$, (of Eq. 1 below) may be essential for accurate thickness measurement in thin material targets.

Referring again to FIG. 1, the Transmit Element side of the Transducer 101 generates an ultrasonic energy wave after being excited by electrical signals at its Input Connector 105 by measurement device 111. The Ultrasonic Energy Wave will hereby be referred to as Wave.

Referring to FIG. 3, the Wave 108 generated by the Transmit Element 101, travels through the Transmit Delay Material 100 and into the coupled target material, such as 107 or 207, through front-surface 110. The Wave is then reflected from the coupled target back-surface 109 and back through front-surface 110 and Receive Delay Material 106 into the Receive Element 104, where it is converted back to an electrical signal.

As can be appreciated by those skilled in the art, the measurement device 111 is capable of precisely measuring the Time Interval (TI) comprised the Time Of Flight (TOF) of each of the elements depicted in FIG. 3, i.e., T1, T2, T3, and T4. It should be noted that the TI measurements associated with T1 and T4 are typically made when transducer 102 is decoupled from the target material and element 101 and 104 are each operated in pulse-echo mode to measure the TI to and from their respective transducer contact surfaces 101a and 104a. Accordingly, the TI values T2 and T3 associated with the target material may be measured because the T1 and T4 are TI components of the total TOF are accounted for.

Therefore, the 'thickness' calculation H for a target material, whether it be a calibration block or test object, may be calculated by Eq. 1 as shown below, $$H=[(TI+t_v)V]/2 \qquad [\text{Eq. 1}]$$

where,

TOF=T1+T2+T3+T4

$t_x$=T1+T4

TI=TOF−$t_x$ $t_v$=V-Path correction factor

V=sound velocity in test blocks 107 and 207.

It should be noted that the above equations are also used to generate the Empirical V-Path Tables typically provided by transducer manufacturers. An Empirical V-Path Table is usually provided for a specific transducer model number.

The preferred embodiment of the present disclosure is a system and method employing a software program that may be used for producing, and employing time distortion correction data in real-time, henceforth referred to as 'V-Path Table' for Transducers that may be employed by ultrasonic thickness measuring apparatus. A key aspect of the present invention includes deriving an 'User Created V-Path Table' and employing such for dual-element transducer calibrations and test object measurement. As further described below, it should be noted that in comparison with the existing Empirical V-Path Table, 'User Created V-Path Table' is derived using TOF data measured for a specific physical transducer. The following method/software program can be used to generate the 'User Created V-Path Table' on any specific transducer and at any point during the service life of the transducer.

Figure 4:
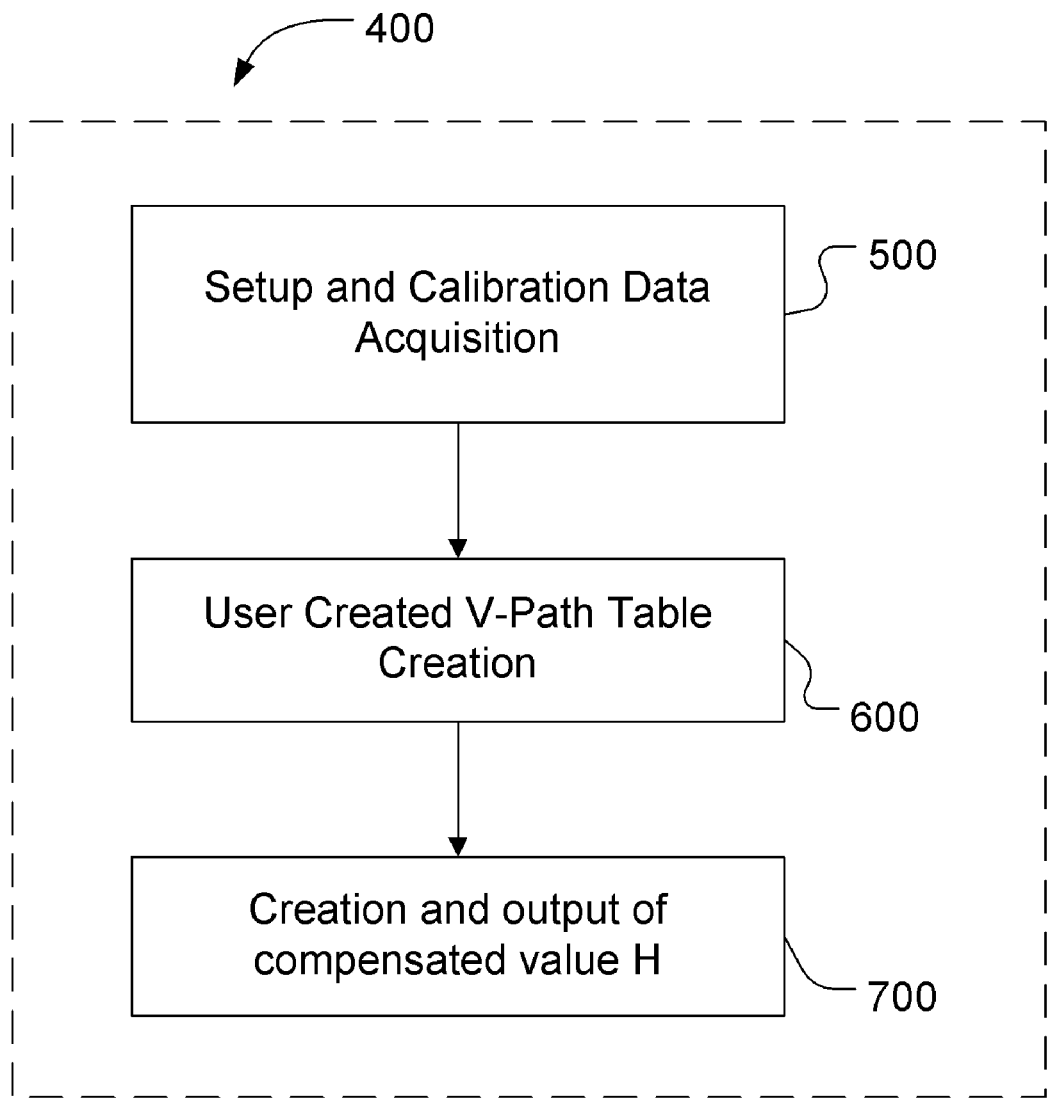
FIG. 4 is a diagram showing the functional modules used for deriving and employing ultrasonic V-Path correction data according to the present invention.

As shown in FIG. 4, the presently disclosed method in combination with a software program performs process 400 that is comprised of modules (or steps) including Setup and Calibration Data Acquisition 500, User Created V-Path Table Creation 600, and Creation and Output of Compensated Value H 700.

Referring now to FIGS. 4, 1 and 2, in step 500, transducer 102 is coupled to a calibration block such as 107 or 207, to acquire the required data elements for the creation of the V-Path table in step 600. Next, in step 700 the V-Path Table is employed during real-time measurement acquisition to correct for time distortion, thereby resulting in a compensated thickness measurement value H. It should be noted that process 400 is performed within inspection device 111 when connected to transducer 106.

It should be noted that the combined 'steps' above are also called modules. The present disclosure is focused on a combination of a software program and a method. The terms 'Step' and 'module' are interchangeably used, wherein 'step' is used in the context of the method and 'module' is used in the context of the system and associated software program.

Figure 5:
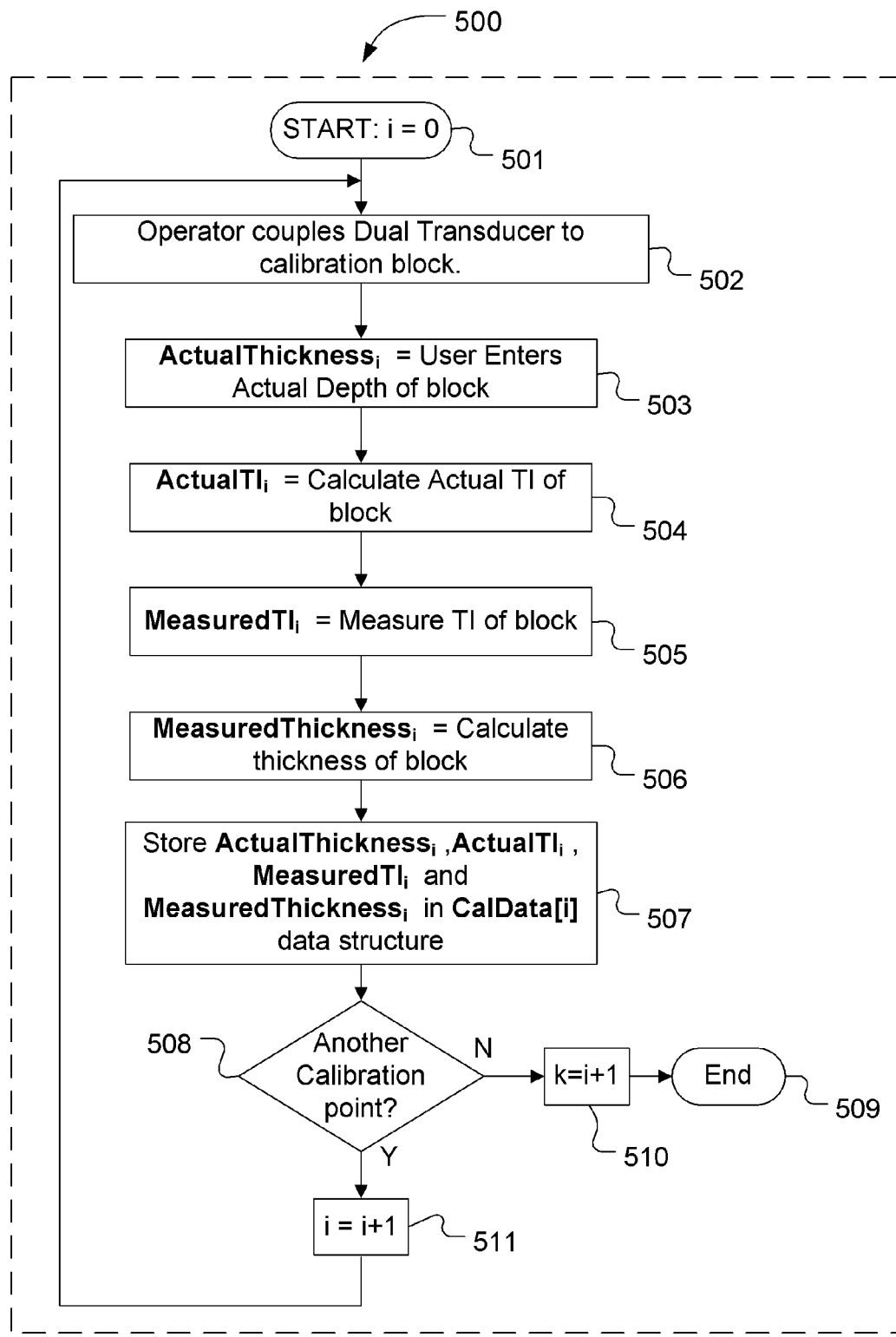
FIG. 5 is a module or component embodiment showing the module and steps required for acquiring input calibration data from the operator.

Turning now to FIG. 5, which provides a more detailed description of the module 500, note that the operator is required to perform a calibration on a range of blocks of different thicknesses. The range or number of thickness points is determined by the operator. After the Setup and Calibration Data Acquisition process within module 500 is completed, the resulting data is provided to the module 600 of FIG. 6 to derive the V-Path Table. The data in the V-Path Table is then used in module 700 of FIG. 7 wherein it may be utilized in the calculation of compensated measurement H to yield an accurate thickness as shown in Eq. 1.

It should be noted that the term "actual" as used in the present disclosure denotes the precise metrics of the target material, and the term 'measured' denotes the metrics of the target material acquired by the measurement device 111. In step 502, the operator couples the transducer 102 to the calibration block and enters the actual thickness of the block in step 503. The actual TI is then calculated in step 504 using Eq. 2 shown below.

$$ActualTI_i = [ActualThickness_i/V]*2 \qquad [Eq.\ 2]$$

where,
V=Material Velocity of the block

The measurement device 111 then acquires the TI in step 505 (FIG. 5), where the measured time is calculated using Eq. 3 shown below.

$$MeasuredTI_i = T2+T3 \qquad [Eq.\ 3]\ (see\ FIG.\ 3)$$

The measured thickness is calculated in step 506 by Eq. 4 shown below.

$$MeasuredThickness_i = [MeasuredTI_i * V]/2 \qquad [Eq.\ 4]$$

where
V=Material Velocity of the block

The data obtained for $ActualTI_i$, $ActualThickness_i$, $MeasuredTI_i$ and $MeasuredThickness_i$ are then stored into CalData[i] in step 507, as multiple-element array or array of data structures. The procedure repeats steps 502 through 508 until the desired range of calibration thicknesses have been entered. The module in FIG. 5 is completed in step 509.

Figure 6:
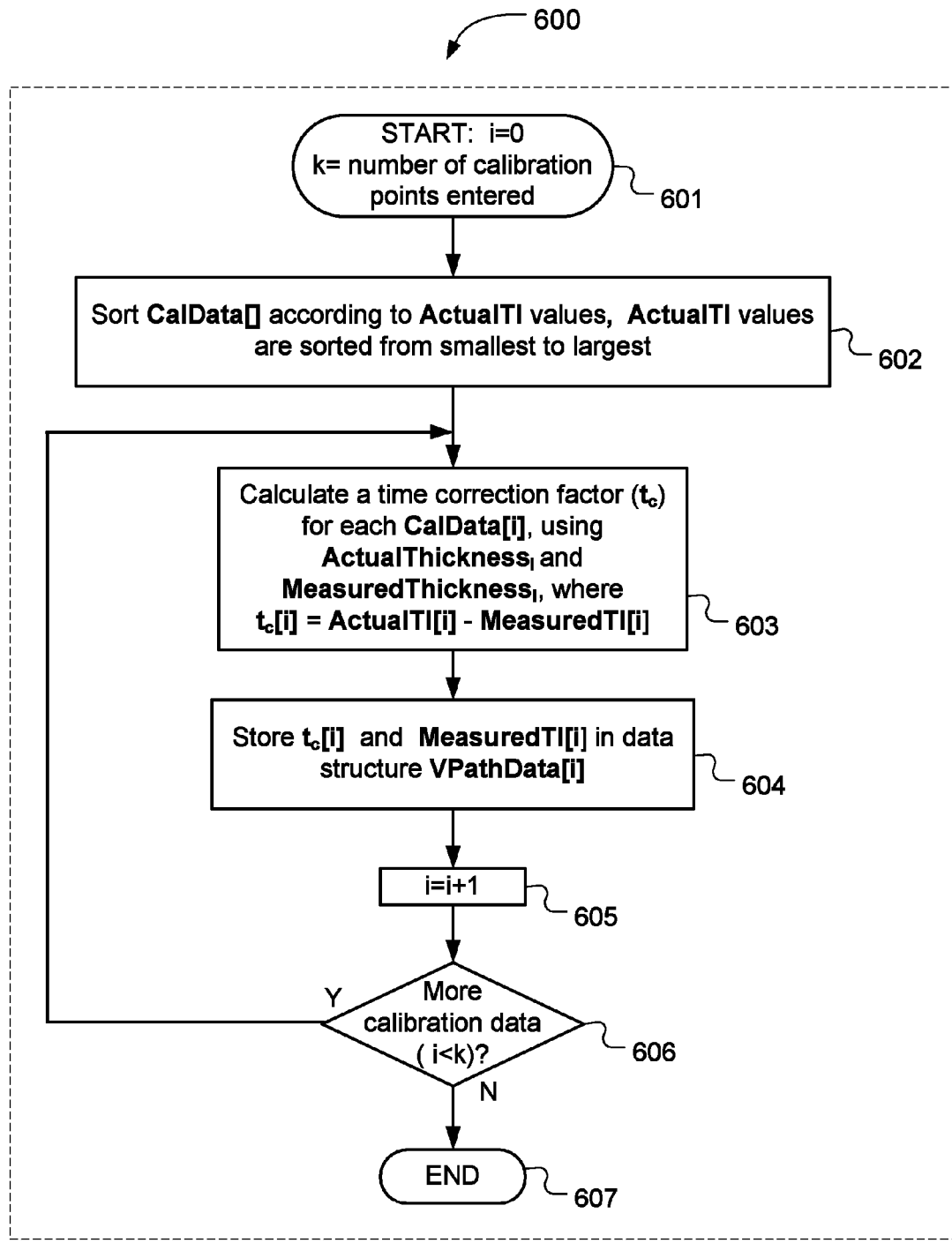
FIG. 6 is a module or component of the embodiment showing the module and steps required for deriving and creating the User Created V-Path correction values.

Reference is now made to FIG. 6, wherein detailed steps of module 600 are elaborated. The CalData[i] data structure is preferably sorted from smallest $ActualTI_i$ value to largest $ActualTI_k$ value in step 602, where k is the number of calibration points entered in step 510 of FIG. 5. Once sorted, a time correction factor is calculated for each calibration point by Eq. 5 shown below.

$$t_c[i] = ActualTI[i] - MeasuredTI[i] \qquad [Eq.\ 5]$$

In practice, $t_c[i]$ and MeasuredTI[i] are stored in step 604 into VPathData[i], which is a multi-element array or array of data structures. The process of calculating $t_c[i]$ and storing it along with MeasuredTI[i] in steps 603 through 606 continues until i=k, where k is the number of calibration points entered in step 510.

Figure 7:
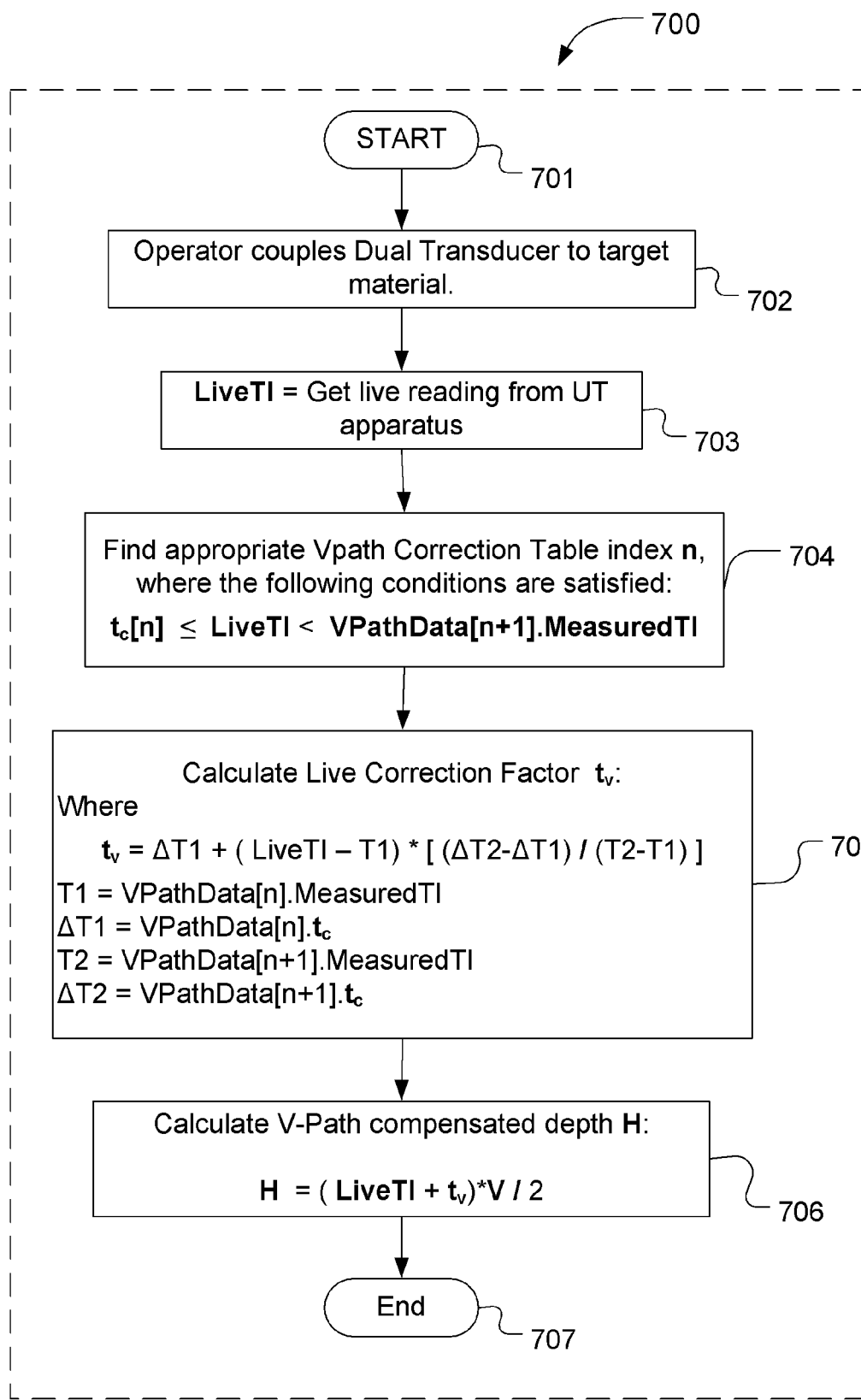
FIG. 7 is a module or component of the embodiment showing the module and steps required for the application of the V-Path correction data during the measurement calculation phase.

Module 700 is now described with reference to FIG. 7. The "User Created V-Path Table" was created as described above within the software program modules 500, and 600, and is then used in module 700 to compensate for time distortion in the thickness measurement of the measurement device 111 and thereby produce V-Path compensated measurement value H.

For module 700, the operator couples the Transducer to the material under test in step 702 and the measurement device 111 acquires a time measurement LiveTI in step 703 using Eq. 6 shown below.

$$LiveTI = T2+T3 \qquad [Eq.\ 6]\ (see\ FIG.\ 3)$$

Figure 8:
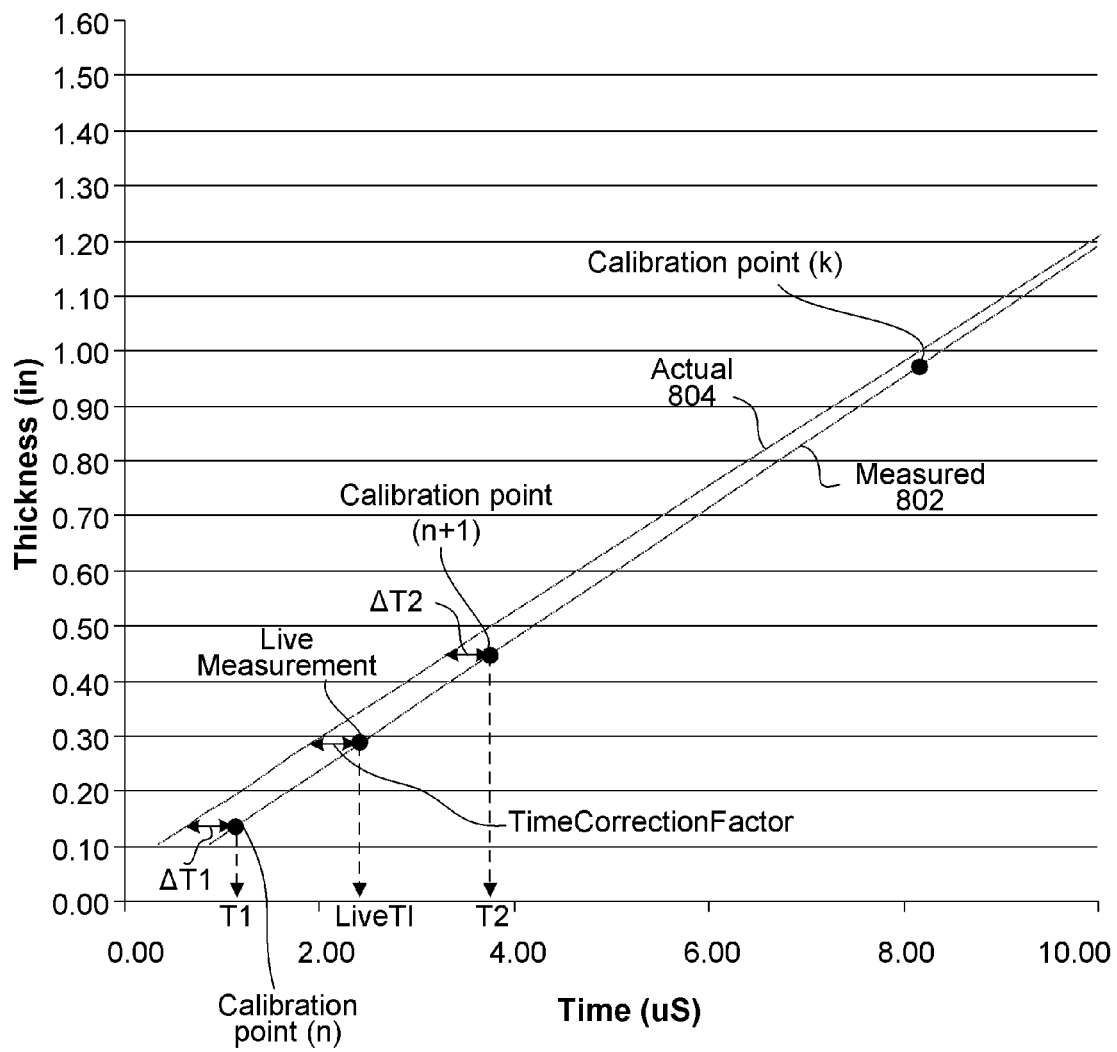
FIG. 8 is a chart showing the Actual Thickness vs. the Measured Thickness by an UT apparatus, and the associated calibration points of the embodiment.

LiveTI is then utilized to determine an index n into VPathData[ ] in step 704 for selecting the appropriate data in the table for that thickness and then using the data for deriving the live (real-time) V-Path correction factor, $t_v$ in step 705 using Eq. 7 shown below.

$$t_v = \Delta T1 + (LiveTI - T1) * [(\Delta T2 - \Delta T1)/(T2-T1)] \qquad [Eq.\ 7]$$

and referring to FIG. 8,
T1=VPathData[n].MeasuredTI, the MeasuredTI value in VPathData[n].
$\Delta T1$=VPathData[n].$t_c$, the $t_c$ value in VPathData[n].
T2=VPathData[n+1].MeasuredTI, the MeasuredTI value in VPathData[n+1].
$\Delta T2$=VPathData[n+1].$t_c$ the $t_c$ value in the VPathData[n+1].

Finally, V-Path compensated measurement value H of the target object is calculated in step 706 by using Eq. 8 shown below.

$$H = [(LiveTI + t_v) * V]/2 \qquad [Eq.\ 8]$$

Figure 9:
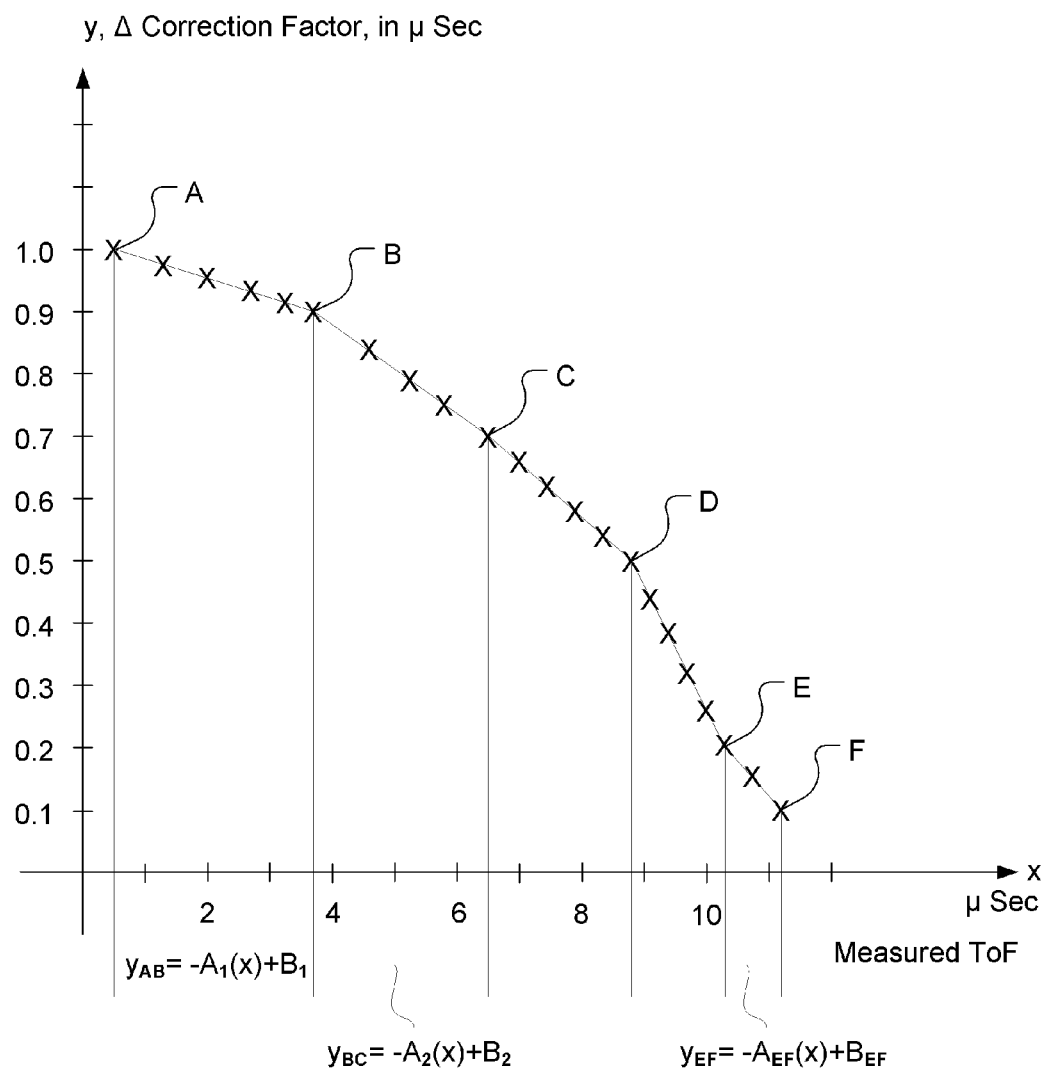
FIG. 9 is a chart showing a plot of time correction factors at different measured wave flight times.

FIG. 8 shows time correction factors designated as $\Delta T1$, $\Delta T2$, etc., at specific calibration points, plotted against the thickness of the test object. It also shows time correction factors for live measurements and identifies them as LiveTI. These "$\Delta$" designated time correction factors can be plotted as shown in FIG. 9, as specific (x,y) coordinate points where, in FIG. 9, the ordinate (y-axis) indicates the time correction factors, at each of the calibration points. The x-axis designates the measured TOF (Time of Flight), at the calibration points.

In the preceding embodiment, time correction factors for the live measurement points are obtained via interpolation calculations, as previously described. See, for example, equation 7. Those skilled in the art appreciate that the plot (FIG. 9) of the actual time correction factors, relative to the measured times at the calibration points, produces a non-linear function, which is not easily fitted to a rigid mathematically expressed formula.

However, in accordance with the presently described alternative embodiment, the software system of the present invention aggregates these discrete data points, for example, between points A and B; B and C; C and D; and D and E, and produces a linear transfer function (formula) for each such section. This allows calculation of the Δ time correction factors, for live measurements, using a specific equation for each section.

Thus, for the Section A-B, the transfer function, i.e. the formula, for calculating the correction factor for the TOF obtained on a test object may be expressed as: $\Delta y_{A-B} = f(\Delta x)$; according to a general form of the equation, which is $y_{A-B} = -A(x) + B$, with A and B being constants which are unique to each of the sections A-B; B-C; etc., in FIG. 9. The variable "x" is the live measured TOF obtained during a test. By adding the thus obtained Δy to the live TOF measurement, one obtains a TOF for thickness values falling on and between the discrete time correction data points, which readily allows calculating the thickness parameter based on the acoustical wave speed through the test object.

The approach of this embodiment does not require accessing the V-Path data tables and calculating interpolated corrections during live measurements on test objects. Instead, it allows the use of direct conversions, using the above formulas.

In creating the segmentized linear transfer functions shown in FIG. 9, it should be noted that the software of the present invention uses actual measurement data to determine the starting and ending points for each section of the curve, using well known mean deviation methodologies to enable the fitting of a linear equation over the selected data ranges.

In operation, a TOF measurement is taken. Then, it is determined to which linear segment the measurement TOF value belongs. Lastly, the appropriate equation is used to calculate the TOF correction. As noted above, the calculation of the thickness is then readily obtained.

In an alternate embodiment, V-Path correction data may be determined for a specific physical transducer by some other means than the measurement device 111 and provided to the measurement device 111 to conduct V-Path correction during real-time measurements. One of the other means may be a measurement device 111 other than the one that will be used to conduct the real-time measurements.

In another alternate embodiment, as shown in FIGS. 1, 2 and 3, ID 112 may provide a means of physical probe identification (i.e. a 'probe identifier'), such as a serial number, coupled to measurement device 111 to be used to recall from its memory the V-Path correction data table associated with the probe identifier. ID 112 may be a non-volatile (NV) digital memory device or a component that maintains a substantially constant value over time—such as a resistor. ID 112 is preferably packaged in an integral manner with probe 102 in order to ensure that ID 112 remains with the probe. For example, ID 112 may be packaged with the probe, the probe cable assembly, or any other device attached to probe 102 on a permanent or semi-permanent basis.

If ID 112 is a NV digital memory device of adequate capacity, the V-Path correction data table may be stored with the physical probe it applies to (i.e. 'V-Path stored in probe'), thereby allowing the probe to be used with any measurement device 111 without the need for the measurement device 111 to store a database of V-Path correction data tables associated with probe identifiers.

The primary advantage provided by the 'probe identifier' and 'V-Path stored in probe' embodiments is improved inspection process efficiency by eliminating the need to perform the V-Path correction data table calibration process before starting an inspection measurement session.

Although these embodiments are described in relation to a V-Path correction data table associated with a specific physical probe, V-Path correction data may also be created by empirical means, such as derivation from a sample population of probes. Analytical means may be used as well, such as a mathematical model of a distinct probe type.

It should be noted with respect to these embodiments that the V-Path correction data table stored in the NV digital memory device may be updated by the user from time to time to account for changes in physical probe properties, thereby maintaining optimal accuracy of the V-Path correction data.

Other arrangements of embodiments of the invention include software programs to perform the method embodiment steps and operations summarized above and disclosed in detail below. More particularly, a computer program is one embodiment that has a computer-readable medium including computer program logic encoded thereon that when encoded and executed in a computerized device provides associated operations providing V-Path error calibration as explained herein. The computer program logic, when executed on at least one processor with a computing system, causes the processor to perform the operations (e.g., the methods and algorithms) indicated herein as embodiments of the invention. Such arrangements of the invention are typically provided as software, code and/or other data structures arranged or encoded on a computer readable medium such as but not limited to an optical medium (e.g., CD-ROM, DVD-ROM, etc.), floppy or hard disk, a so-called "flash" (i.e., solid state) memory medium, or other physical medium, such as but not limited to firmware or microcode in one or more of ROM or RAM or PROM chips, or as an Application Specific Integrated Circuit (ASIC) or as downloadable software images in one or more modules, shared libraries, etc. The software or firmware or other such configurations can be installed onto a computerized device to cause one or more processors in the computerized device to perform the techniques explained herein as embodiments of the invention. Software processes that operate in a collection of computerized devices, such as in a group of data communications devices or other entities may also provide the system of the invention. The system of the invention may be distributed between many software processes on several data communications devices, or all processes may run on a small set of dedicated computers, or on one computer alone.

It is to be understood that embodiments of the invention may be embodied strictly as a software program, as software and hardware, or as hardware and/or circuitry alone. The features disclosed and explained herein may be employed in computerized devices and software systems for such devices such as those manufactured by Olympus NDT Inc. of Waltham, Mass.

Although the present invention has been described in relation to particular exemplary embodiments thereof, many other variations and modifications and other uses will become apparent to those skilled in the art. It is preferred, therefore, that the present invention not be limited by the specific disclosure.

What is claimed is:

1. A thickness measuring system for measuring thicknesses of test objects, comprising:
   a probe configured to launch acoustical waves into a test object, to receive returning waves and to produce an electrical output representative of the returning waves;
   a calibration module configured to provide V-Path time of flight (TOF) correction data over a plurality of object thickness points, obtained from one or more objects having known thicknesses, using the same physical probe as is used for said measuring;
   a control and computation unit, coupled to the probe and configured to compute a time of flight value of the acoustical waves launched by the probe; and
   a correction module associated with the unit and configured to receive the V-Path TOF correction data from the calibration module and to correct the time of flight computed by the unit based on the V-Path TOF correction data provided by the calibration module.

2. The thickness measuring system of claim 1, in which the probe is a dual element probe.

3. The thickness measuring system of claim 1, in which the V-Path TOF correction data is provided in the form of a plurality of discrete correction values, and wherein the unit is configured to correct the measured TOF value by locating a corresponding discrete TOF correlation data and/or by computing a correction TOF data by interpolation using adjacent ones of V-Path correction data.

4. The thickness measuring system of claim 3, in which an object thickness H of the test object is obtained using the following equations:

$$H=[(LiveTI+t_v)*V]/2$$

Where $$t_v=\Delta T1+(LiveTI-T1)*[(\Delta T2-\Delta T1)/(T2-T1)]$$

Where
   T1=VPathData[n].MeasuredTI
   ΔT1=VPathData[n].$t_c$
   T2=VPathData[n+1].MeasuredTI
   ΔT2=VPathData[n+1].$t_c$
Where $$t_c[n] \leq LiveTI < VPathData[n+1].MeasuredTI.$$

5. The thickness measuring system of claim 1, in which the V-Path TOF correction data for each object thickness are obtained by repeated measurements and by the averaging of repeated measurements at the same thickness.

6. The thickness measuring system of claim 1, wherein the corrected times of flight are derived from linear equations which are fitted to the V-Path TOF correction data.

7. The thickness measuring system of claim 1, wherein the calibration module comprises a data table.

8. The thickness measuring system of claim 1, wherein the system is configured to perform non-destructive testing to monitor the structural integrity of the test objects.

9. The thickness measuring system of claim 1, including TOF probe identification data of said probe and a memory storing multiple TOF correction data for a plurality of probes, each TOF correction data being identified by a corresponding TOF probe identification data.

10. The thickness measuring system of claim 1, including a memory integrated with said probe which stores said TOF correction data therein.

11. A method of measuring the thicknesses of test objects, comprising:
   launching acoustical waves into a test object with a probe and receiving returning waves and producing an electrical output representative of the returning waves;
   collecting and providing V-Path time of flight (TOF) correction data over a plurality of object thickness points, and obtaining the same from one or more objects having known thicknesses, using the same physical probe as is used for said measuring;
   computing a time of flight value of the acoustical waves launched by the probe; and
   using the V-Path TOF correction data and correcting the time of flight that has been computed, based on the V-Path TOF correction data obtained relative to the objects having known thicknesses.

12. The method for claim 11, further including providing the V-Path time of flight correction data in the form of a plurality of discreet correction values and using interpolation to correct the time of flight computed for the test object.

13. The method of claim 11, including calculating an object thickness H of the test object using the following equations:

$$H=[(LiveTI+t_v)*V]/2$$

Where $$t_v=\Delta T1+(LiveTI-T1)*[(\Delta T2-\Delta T1)/(T2-T1)]$$

Where
   T1=VPathData[n].MeasuredTI
   ΔT1=VPathData[n].$t_c$
   T2=VPathData[n+1].MeasuredTI
   ΔT2=VPathData[n+1].$t_c$
Where $$t_c[n] \leq LiveTI < VPathData[n+1].MeasuredTI.$$

14. The method of claim 11, including obtaining the V-Path TOF correction data for each object thickness by repeated measurements and by averaging the repeated measurements at the same thickness points.

15. The method of claim 11, including calculating the corrected times of flight from linear equations which have been pre-fitted to the V-Path TOF correction data.

16. The method of claim 11, including performing non-destructive testing of the test object to monitor the structural integrity thereof by measuring the thickness of the test object at various locations thereon.

17. The method of claim 11, further including obtaining the V-Path TOF correction data by reading TOF probe identification data associated with said probe being used, and selecting said V-Path TOF correction data associated with said probe from a memory containing V-Path correction data for a plurality of probes.

18. The method of claim 11, including storing said V-Path TOF correction data in a memory module integrated with said probe.

19. A method of measuring the thicknesses of test objects, comprising:

launching acoustical waves into a test object with a probe and receiving returning waves and producing an electrical output representative of the returning waves;

collecting and providing V-Path time of flight (TOF) correction data over a plurality of object thickness points, and obtaining the same from one or more objects having known thicknesses, using one or more probes having characteristics similar to said probe used for said measuring;

computing a time of flight value of the acoustical waves launched by the probe; and using the V-Path TOF correction data and correcting the TOF value that has been computed, based on the V-Path TOF correction data obtained relative to the object or objects having known thicknesses.

* * * * *